United States Patent
Fu et al.

(10) Patent No.: US 8,569,075 B2
(45) Date of Patent: Oct. 29, 2013

(54) RADIOIMMUNOASSAY WITH A 96-WELLED MICRO-PLATE

(75) Inventors: Meng-Jun Fu, Taoyuan County (TW);
Ping-Hung Yu, Taoyuan County (TW);
Chin-Yan Tsai, Taoyuan County (TW);
Kuan-Yin Chen, Taoyuan County (TW);
Chia-Chieh Chen, Taoyuan County (TW)

(73) Assignee: Atomic Energy Council Energy—Institute of Nuclear Energy Research, Lungtan, Taoyuan (TW)

( * ) Notice: Subject to any disclaimer, the term of this patent is extended or adjusted under 35 U.S.C. 154(b) by 218 days.

(21) Appl. No.: 13/232,928

(22) Filed: Sep. 14, 2011

(65) Prior Publication Data
US 2013/0065322 A1    Mar. 14, 2013

(51) Int. Cl.
*G01N 33/543*    (2006.01)

(52) U.S. Cl.
USPC ..... 436/518; 422/407; 435/288.3; 435/288.4; 436/804; 436/809

(58) Field of Classification Search
USPC ............. 422/407; 435/288.3, 288.4; 436/809, 436/518, 804
See application file for complete search history.

(56) References Cited

U.S. PATENT DOCUMENTS

| | | | | |
|---|---|---|---|---|
| 3,790,663 | A | * | 2/1974 | Garrison et al. ............... 436/531 |
| 4,276,259 | A | * | 6/1981 | Eibl et al. .......................... 422/71 |
| 4,895,706 | A | * | 1/1990 | Root et al. ...................... 422/534 |
| 5,084,246 | A | * | 1/1992 | Lyman et al. .................. 422/534 |
| 5,110,556 | A | * | 5/1992 | Lyman et al. .................. 422/552 |
| 6,632,624 | B1 | * | 10/2003 | Degorce et al. .............. 435/7.92 |

* cited by examiner

*Primary Examiner* — Chris L Chin
(74) *Attorney, Agent, or Firm* — Jackson IPG PLLC

(57) ABSTRACT

A method for using a multi-welled micro-plate in radioimmunoassay ("RIA") is disclosed to improve the performance of RIA. At first, there is provided a multi-welled micro-plate that can be dismantled and divided into multiple wells. Then, samples are filled into the wells of the multi-welled micro-plate for incubation. Washing, tracer-adding, incubation, and washing are executed. At a final step, the multi-welled micro-plate is separated into wells, and each of to the wells is put into a test tube for gamma counting by a gamma counter.

1 Claim, 1 Drawing Sheet

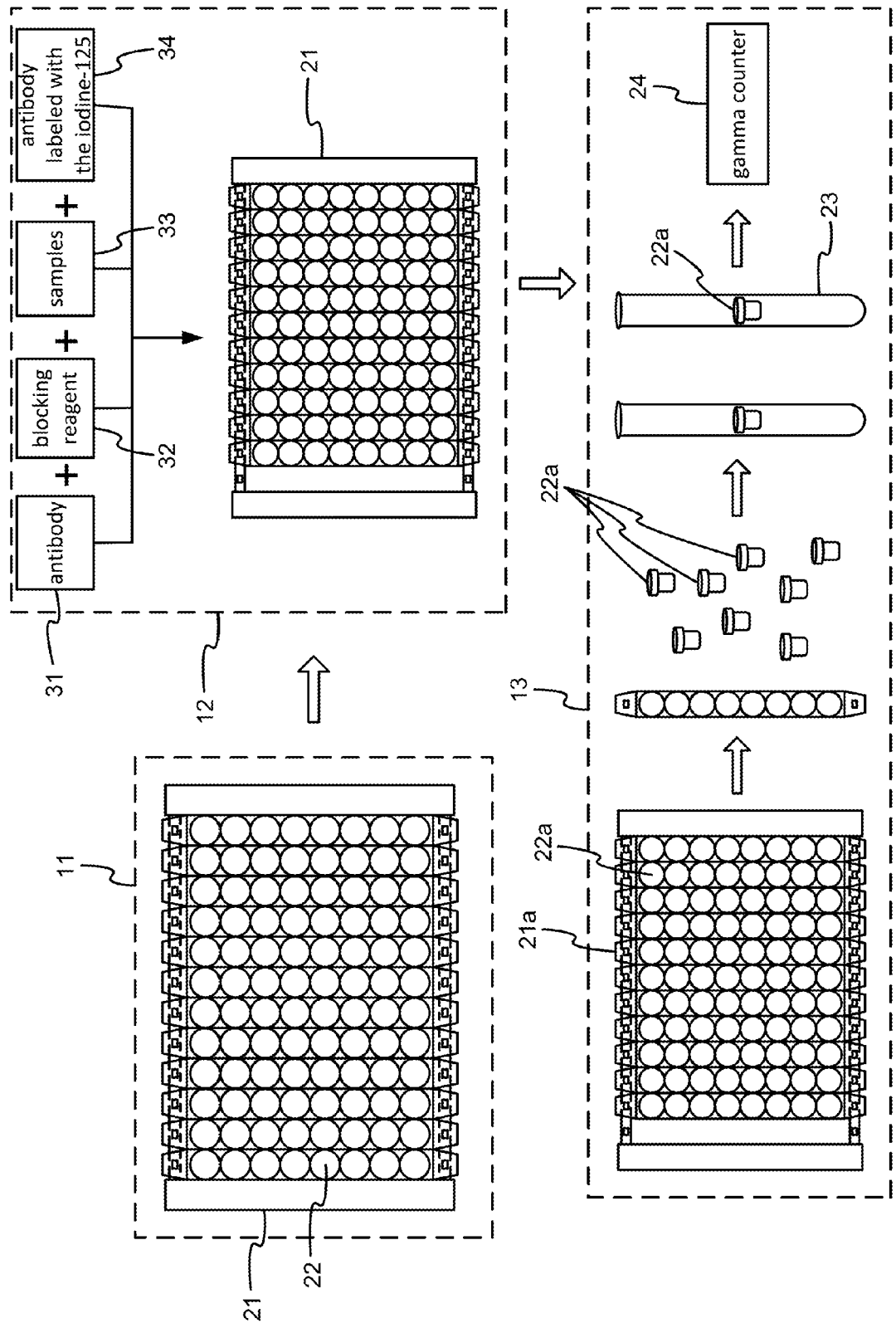

RADIOIMMUNOASSAY WITH A 96-WELLED MICRO-PLATE

BACKGROUND OF INVENTION

1. Field of Invention

The present invention relates to radioimmunoassay and, more particularly, to use of a 96-welled micro-plate in radioimmunoassay.

2. Related Prior Art

Radioimmunoassay ("RIA") was developed by Yalow and Berson in 1959 for measuring the concentration of the insulin in the blood of a diabetic patient. In typical radioimmunoassay, a target material to be measured is used as an antigen for producing an antibody. The antibody is attached to a test tube. A purified standard of the target material is labeled with iodine-125 as a tracer. A sample of the target material and the labeled standard of the target material are filled in the test tube for incubation. The target material in the sample and the standard of the target material labeled with the iodine-125 compete against each other to bind to the antibody attached to the test tube. If the concentration of the target material in sample is high, the binding amount of the standard labeled with the iodine-125 is low. Therefore, in radioactive counting, the value is low if the concentration of the target material in the sample is high, and the value is high if the concentration of the target material in the sample is low.

The typical radioimmunoassay is often conducted in a single test tube as discussed above. A layer of an antibody is coated on an internal side of the test tube. A sample of a target material is filled in the test tube for incubation so that the antibody binds the target material in the sample. Other materials are washed away after the target material is binding to the antibody. Then, the standard of the target material is labeled with a radionuclide and filled in the test tube for competition with the target material. Later, an excessive portion of the sample of the target material labeled with the radionuclide is washed away. The concentration of the target material in the sample is learned from the radioactive reading in radioactive counting. The radionuclide is generally iodine-125 and the radioactive counting is therefore based on gamma ray. However, gamma ray will penetrate, and therefore a reader can only be used to read only one test tube. To use a single test tube in such an experiment is not without any problem. As radioimmunoassay was developed long time ago, and only a few automatic or semiautomatic instruments have been devised since. The price of such an automatic or semiautomatic instrument is expensive and imposes a heavy financial burden on a user. To operate the tube manually without using any automatic or semiautomatic instrument is however limiting regarding the rate of the handling of samples. On the other hand, should a 96-welled micro-plate be used in an experiment, the radioactive reading of the gamma ray in a well would be interfered with by the gamma ray in another well.

There has been an attempt to use a multi-welled micro-plate in typical radioimmunoassay. Small plastic balls are coated with an antibody before they are located in the multi-welled micro-plate for incubation. After the incubation, the small plastic balls are transferring to test tubes for radioactive counting. This method has rarely been used, and related instruments are also rare and expensive.

If the nuclide that radiates gamma ray is replaced with a nuclide that radiates beta ray such as $_3H$ for radioimmunoassay, a 96-welled micro-plate can be used. Accordingly, liquid scintillation analysis is used. Beta ray is not strong and does not penetrate the wells of the 96-welled micro-plate which is generally made of a plastic material. Hence, the radioactive reading of the beta ray in a well is not interfered with by the beta ray in another well. In the radioactive counting, scintillation liquid is filled in the wells and reacted with the beta ray so that photons are emitted. A liquid scintillation analyzer related to the 96-welled micro-plate is used to measure the readings of the beta ray in the wells. The use of a beta ray-radiating nuclide in radioimmunoassay is however not popular in comparison with iodine-125.

There has been developed another method that can be used to measure the concentration of the insulin in the blood of a diabetic patient, i.e., immunoradiometric assay ("IRMA"). In typical immunoradiometric assay, a target material to be measured is used as an antigen for producing capture antibody and detection antibody. The two antibodies recognize different epitopes of the antigen. At first, the capture antibody is attached to a test tube while the detection antibody is labeled with iodine-125. Later, a sample of the target material (antigen) is filled in the test tube for incubation. Now, the antigen in the sample is binding to the capture antibody in the test tube. Then, the detection antibody is filled in the test tube. The detection antibody recognizes the antigen binding to capture antibody. In radioactive counting, the concentration of the target material in the sample is high as the amount of the detection antibody binding in the test tube is large. Therefore, the concentration of the target material in the sample is in positive proportion with the radioactive reading. This method is sometimes called the "sandwich method."

The present invention is therefore intended to obviate or at least alleviate the problems encountered in prior art.

SUMMARY OF INVENTION

It is the primary objective of the present invention to provide a simple, practical, inexpensive, efficient method for radioimmunoassay using a 96-welled micro-plate.

To achieve the foregoing objective, the method includes the steps of providing a multi-welled micro-plate, executing radioimmunoassay, and executing gamma counting. The multi-welled micro-plate can be dismantled and divided into wells. The step of executing radioimmunoassay includes the steps of filling an antibody in the wells of the multi-welled micro-plate so that the antibody is coated on an internal side of each of the wells of the multi-welled micro-plate, washing away an excessive portion of the antibody from the wells, coating an blocking reagent on a portion of the surface of the multi-welled micro-plate that is not covered by the antibody, removing an excessive portion of the blocking reagent, filling samples of a target material in the wells, oscillating the multi-welled micro-plate for a predetermined period of time, washing away an excessive portion of the samples with washing buffer for several times, labeling an antibody with iodine-125 and filling it in the wells, oscillating the multi-welled micro-plate for another predetermined period of time, washing away an excessive portion of the antibody labeled with the iodine-125 by washing buffer for several times, and inverting and locating the multi-welled micro-plate on a tower of tissue paper so that all liquid leaves the wells. The step of executing gamma counting includes the steps of dismantling the multi-welled micro-plate into separate wells, casting each of the wells in a test tube, providing a gamma counter for the gamma counting in the test tubes, thus measuring the concentrations of the target material in the samples Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein:

FIG. 1 is a flow chart of method for radioimmunoassay using a 96-welled micro-plate according to the preferred embodiment of the present invention.

DETAILED DESCRIPTION OF PREFERRED EMBODIMENT

Referring to FIG. 1, there is shown a method for radioimmunoassay using a 96-welled micro-plate according to the preferred embodiment of the present invention. At 11, there is provided a 96-welled micro-plate 21 that can be dismantled. The 96-welled micro-plate 21 includes twelve rows each including eight wells 22.

At 12, radioimmunoassay is conducted. An antibody 31 is filled in the wells 22 of the 96-welled micro-plate 21 so that the antibody 31 is coated on an internal side of each of the wells 22 of the 96-welled micro-plate 21. An excessive portion of the antibody 31 is washed away from the wells 22 before an blocking reagent 32 is coated on a portion of the 96-welled micro-plate 21 that is not covered by the antibody 31. An excessive portion of the blocking reagent 32 is removed before samples 33 of a target material are filled in the wells 22 by a pipetter for example. Then, oscillation is conducted for a predetermined period of time before an excessive portion of the samples 33 is washed away by washing buffer such as water for several times. An antibody 34 is labeled with iodine-125 and filled in the wells 22 for oscillation and incubation for another predetermined period of time. An excessive portion of the antibody 34 labeled with the iodine-125 is washed away by washing buffer such as water for several times. Then, the 96-welled micro-plate 21a is inverted and located on a tower of tissue paper for example so that no liquid is left in the wells 22.

At 13, the 96-welled micro-plate 21 is dismantled and gamma counting is conducted. The 96-welled micro-plate 21 is divided into twelve rows and each of the rows is divided into eight wells 22. Each of the wells 22 is cast in a test tube 23. Then, a gamma counter 24 is used for the gamma counting in the test tubes 23. Thus, the concentrations of the target material in the samples 33 are measured. The test tubes 23 are those that are used for typical radioimmunoassay.

As described above, in the radioimmunoassay of the present invention, the 96-welled micro-plate 21 is used instead of the single test tube used in the typical radioimmunoassay discussed in the Related Prior Art. The rate for the handling of samples 33 is increased while the cost of the automation is reduced. It should however be noted that the 96-welled micro-plate 21 is a special model that can be dismantled. The provision of the samples 33, incubation, washing, and the provision of the tracer such as iodine-125 are identical to those conducted in the typical radioimmunoassay. Finally, the 96-welled micro-plate 21 is dismantled and divided into ninety-six wells 22 and each of the wells 22 is cast in a test tube 23 for the gamma counting.

The present invention exhibits several advantages over the prior art.

At first, as the 96-welled micro-plate 21 is used in the radioimmunoassay, automatic or semiautomatic instruments such as a pipette, an oscillator and a micro-plate washer can be used together with the 96-welled micro-plate 21 for efficient operation.

Secondly, any currently available instruments that can be used together with a typical 96-welled micro-plate can be used together with the 96-welled micro-plate 21 of the present invention, which can be divided into the wells 22. In comparison with development of automatic or semiautomatic instruments for use with test tubes, it is inexpensive to develop automatic or semiautomatic instruments for use with the 96-welled micro-plate 21 since there are many manufacturers who make such automatic or semiautomatic instruments competing against one another.

Thirdly, the 96-welled micro-plate 21 is more compact than ninety-six test tubes would be.

Fourthly, with the 96-welled micro-plate 21, the processing of a large number of samples is efficient.

Fifthly, the finishing of the internal side of each of the wells 22 of the 96-welled micro-plate 21 is advanced. It is possible to finish the internal side of each of the wells 22 so that it can seize the antigen or antibody by covalent bonds. On the contrary, it is only possible to finish an internal side of a test tube so that it can seize the antibody or antigen by hydrogen bonds or van der Waal's forces. With covalent bonds, the wells 22 can seize molecules that cannot easily be attracted otherwise. Covalent bonds are strong and can be washed with strong cleaning materials. With covalent bonds, non specific binding is suppressed. Therefore, the performance of the radioimmunoassay is improved because of the use of the 96-welled micro-plate 21.

Sixthly, 96-welled micro-plates have been made and used for years. It would not be difficult or expensive to develop the 96-welled micro-plate 21 of the present invention.

Seventhly, the design of the present invention is simple, and the use of the present invention is therefore easy.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. A method for radioimmunoassay for measuring concentrations of a target material in samples including the steps of:
   providing a multi-welled micro-plate 21 that can be dismantled;
   executing radioimmunoassay including the steps of:
      filling an antibody 31, specific for the target material, in the wells 22 of the multi-welled micro-plate 21 so that the antibody 31 is coated on an internal side of each of the wells 22 of the multi-welled micro-plate 21;
      washing away an excessive portion of the antibody 31 from the wells 22;
      coating an blocking reagent 32 on a portion of the surface of the multi-welled micro-plate 21 that is not covered by the antibody 31;
      removing an excessive portion of the blocking reagent 32;
      filling samples 33 of a target material in the wells 22;
      oscillating the multi-welled micro-plate 21 for a predetermined period of time;
      washing away an excessive portion of the samples 33 is by washing buffer for several times;
      labeling an antibody 34 specific for the target material with iodine-125 and filling it in the wells 22;
      oscillating the multi-welled micro-plate 21 for another predetermined period of time;
      washing away an excessive portion of the antibody 34 labeled with the iodine-125 by washing buffer for several times; and inverting and locating the multi-welled micro-plate 21 on a tower of tissue paper so that all liquid leaves the wells 22; and executing a gamma counting including the steps of:
- dismantling the multi-welled micro-plate 21 into separate wells 22;
- casting each of the wells 22 in a test tube 23; and
- providing a gamma counter 24 is used for the gamma counting in the test tubes 23, thus measuring the concentrations of the target material in the samples 33.

\* \* \* \* \*